(12) United States Patent
Perovitch et al.

(10) Patent No.: US 7,794,420 B2
(45) Date of Patent: Sep. 14, 2010

(54) AUTOTRANSFUSION METHOD AND AUTOTRANSFUSION DEVICE WITH PHASE SEPARATION AND CONCENTRATION, COMPRISING REMOVABLE BAGS

(75) Inventors: Philippe Perovitch, Lege Cap Ferret (FR); Francis Gadrat, Bordeaux (FR); Bertrand Chastenet, Eysines (FR)

(73) Assignee: Direction et Priorites SA, Gradignan (FR)

( * ) Notice: Subject to any disclaimer, the term of this patent is extended or adjusted under 35 U.S.C. 154(b) by 730 days.

(21) Appl. No.: 11/660,323

(22) PCT Filed: Aug. 4, 2005

(86) PCT No.: PCT/FR2005/050648
§ 371 (c)(1),
(2), (4) Date: Feb. 15, 2007

(87) PCT Pub. No.: WO2006/021728
PCT Pub. Date: Mar. 2, 2006

(65) Prior Publication Data
US 2008/0058695 A1 Mar. 6, 2008

(30) Foreign Application Priority Data
Aug. 19, 2004 (FR) .................................. 04 51870

(51) Int. Cl.
*A61M 37/00* (2006.01)
*A61M 1/36* (2006.01)

(52) U.S. Cl. .................. 604/7; 604/4.01; 604/6.09; 422/44

(58) Field of Classification Search ............... 604/4.01, 604/5.01, 5.04, 6.01, 6.09, 6.1, 6.11, 7–9; 210/645, 781, 782; 422/44
See application file for complete search history.

(56) References Cited

U.S. PATENT DOCUMENTS

| 4,006,745 | A | * | 2/1977 | Sorenson et al. ........... 604/6.15 |
| 4,631,050 | A | * | 12/1986 | Reed et al. ................. 604/6.09 |
| 4,886,487 | A | * | 12/1989 | Solem et al. ............... 604/6.07 |
| 4,892,529 | A |   | 1/1990 | Valerio et al. |
| 5,215,519 | A | * | 6/1993 | Shettigar ................... 604/6.09 |

FOREIGN PATENT DOCUMENTS

| DE | 297 13 774 | 1/1998 |
| EP | 0 525 493 | 2/1993 |

\* cited by examiner

*Primary Examiner*—Leslie R Deak
(74) *Attorney, Agent, or Firm*—Young & Thompson

(57) ABSTRACT

A process for treating the hemorrhage fluids of a patient at the time of a surgical procedure with the aim of carrying out an autotransfusion, includes a stage for recovering the hemorrhage fluids with simultaneous introduction of agents such as anticoagulant and/or diluting agents, at least one stage for the mechanical separation/concentration of this hemodiluted hemorrhage fluid in order to concentrate its content in red blood cells and partially purify it, this phase being collected in a sterile manner so as to be fit for injecting back to the patient. Also described is the related device.

20 Claims, 3 Drawing Sheets

AUTOTRANSFUSION METHOD AND AUTOTRANSFUSION DEVICE WITH PHASE SEPARATION AND CONCENTRATION, COMPRISING REMOVABLE BAGS

BACKGROUND OF THE INVENTION

The present invention covers an autotransfusion process and an autotransfuser device with separation of aqueous and blood phase and removable bags.

A highly performing single use autotransfuser device is known and has been the object of an application for a French patent under No 2 600 537.

Such an autotransfuser device is particularly useful in certain circumstances when known hospital procedures are inappropriate. It is well recognized that in case of a delicate surgical procedure, whether due to length or high risk of haemorrhage, practitioners organize for appropriate quantities of blood.

This type of practice is admissible for planned procedures, in medically equipped sites, and close to properly supplied blood banks.

Nevertheless, one can remark on the high cost and sometimes difficult supply especially for some more specific blood groups. Moreover, once the blood has been delivered, stocks unused during the procedure cannot be kept for long, presently not beyond 35 days, thus requiring the proper management of dates and generating heavy administrative constraints for medical centres whose vocation this is not.

It is also known that in some countries, it is difficult in the case of a blood transfusion to have any certainties as to the quality and purification_of the blood, which puts transfused patients at risk. There could in particular be potential contamination with HIV virus, hepatitis, tuberculosis or syphilis, as well as with undetected or undetectable pathogens such as non conventional pathogens.

Moreover, in case of transfusion, it is more judicious to recover and transfuse back at least part of an individual's own blood, with his or her antibodies and all of his or her other molecules, rather than injecting him or her with blood from a blood bank.

There are also other situations, especially natural disasters or war situations, when the supply of blood is made impossible by the actual quantities required. Autotransfusion then remains the only solution.

Some populations do not accept to be transfused with blood from another person for religious reasons, personal convictions or other reasons. Once again, in such cases autotransfusion is the only way of saving lives.

It is necessary to recall as well that in the case of accidents, the time available for intervention can be very short and in such short intervals, supply from a blood bank is extremely difficult not to say impossible, especially so in countries without the organizations or structures for collecting, controlling and implementing blood transfusion. In such cases, autotransfusion with the recovery of haemorrhage blood represents an option which is immediately available.

It is necessary to distinguish two special applications, the first one intra operative and the second post operative, some procedures being concerned by both applications, with an autotransfusion during the procedure which is continued after the procedure through the recovery of the haemorrhaged blood with an outside drain, usually during the 6 hours following the procedure.

In the case of the intra operative transfusion, it is necessary to be able to reinject the recovered blood directly to the patient, almost in continuous mode. As is known, this blood must necessarily be diluted when collected and anti-coagulant products must be added in order to preserve its transfusional quality.

These actions seem necessary because when using a vector liquid for the haemorrhage blood recovered, the red blood cells can thus be protected from direct physical traumas when coming into mechanical contact with filters and other tubing. This dilution in a vector liquid also reduces the contact of red blood cells with air thus restricting their haemolysis significantly. The recovered blood must then be reinjected into the patient's body but there are some major issues to be faced.

In the case of over diluted blood one may cause hypervolemia phenomena due to these overly important transfused liquids and hypocoagulability due to the transfusion of an excess of anti-coagulant products.

In order to avoid this occurrence, it is necessary to use extremely complex and expensive equipment to extract the haemodilution liquids, called washing/centrifugal machines.

Moreover, when carrying out an autotransfusion with blood that has been extracted directly and only diluted and complemented with anti-coagulant products, there is a risk of injecting activated or degraded biological substances likely to produce side effects. On might find histamines, kallicreins or kinins, more or less degraded plasma factors, which it is better to remove or else small proteins issued from cell traumas.

SUMMARY OF THE INVENTION

Intra operatively, the process of this invention thus consists in recovering the blood, diluting it and injecting it with anticoagulant products simultaneously at the time of collection and in proportion with the quantity collected and then filtering it and separating the liquid phase from that containing the red blood cells thus enabling on the one hand a concentration of the latter phase to be reinjected and on the other hand a recovery of the liquid phase to be eliminated.

for a post operative intervention, the blood is collected directly with a drain and the liquid thus running is not processed in any way, whether by dilution or addition of anticoagulant products, as in this case it is obviously ready for reinjection provided the collection is carried out under sterile conditions.

This invention proposes a single use device which enables an implementation in intra or post operative conditions, independently, and also the use of the same device in the case of a procedure requiring a continuation of the autotransfusion process from the intra operative into the postoperative stage.

BRIEF DESCRIPTION OF THE DRAWINGS

The procedure and the associated device are now described in details in a specific, non restrictive implementation, with reference to the accompanying drawings, in which.

DETAILED DESCRIPTION OF THE PREFERRED EMBODIMENTS

Figure 1:
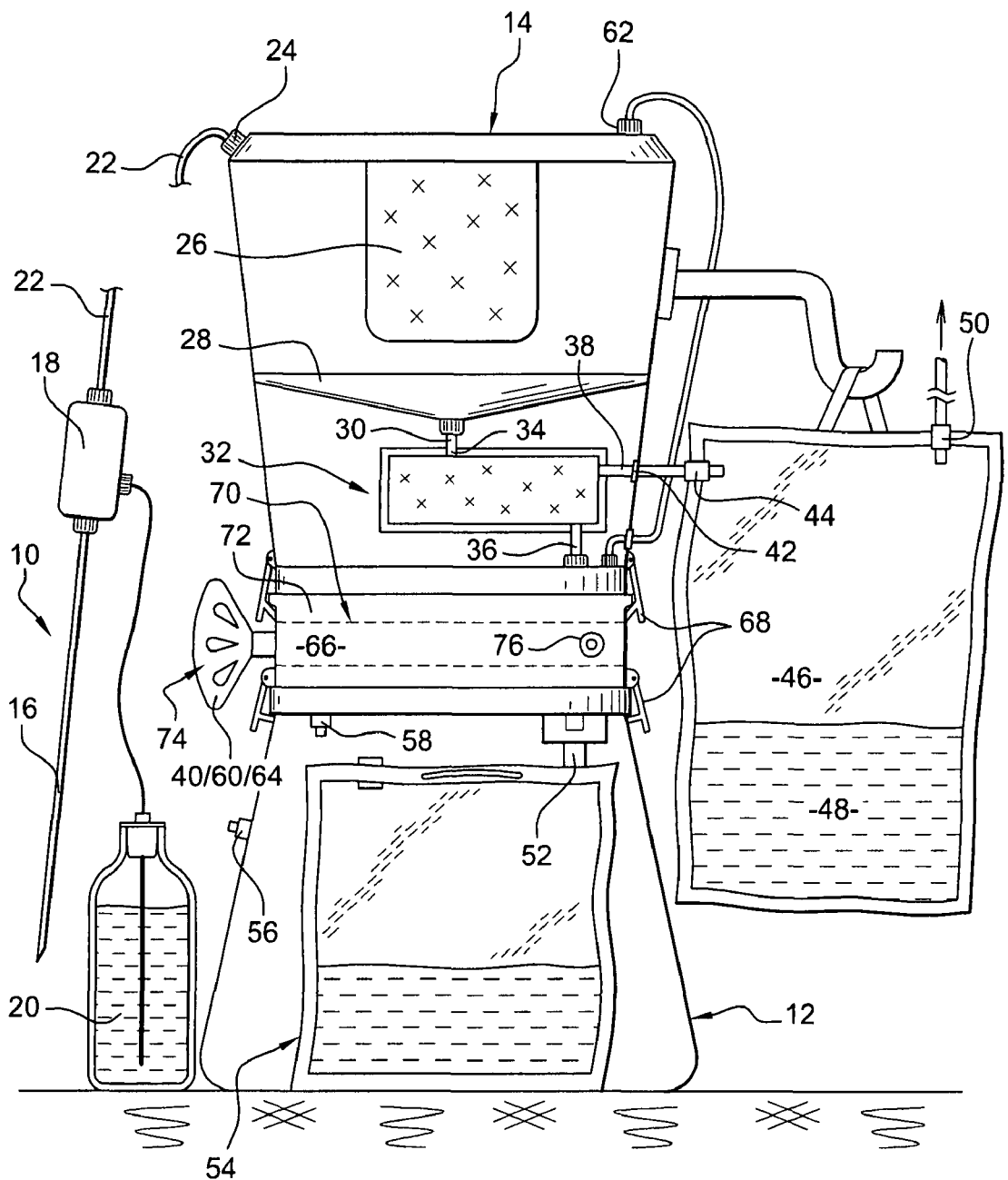
FIG. 1 is a view of the complete device, equipped with its per operative layer.

FIG. 1 represents the means 10 for collecting a patient's blood during a procedure, with the base 12 of the device subject of this invention and a removable head 14 employed for intra operative use according to the invention.

The means 10 used for collecting the blood are known per se and are composed of a suction cannula 16 for haemorrhage blood, integrated means 18 for dosage of diluting and anticoagulant agents 20 and an evacuation tube 22.

The means 28 for dosage enable the continuous addition of the required quantity of diluting and anticoagulant agents 20 in proportion to the blood volume collected.

The evacuation tube 22 is connected to a connection piece 24 at the top of the removable head 14.

This connection piece leads to a filter 26, with a 40 μm mesh to give an idea.

This filter 26 is affixed to the top part of the head 14.

This filter is placed above a funnel-shaped collector 28 with an outlet 30.

A separation/concentration filter 32 is mounted on this outlet by means of its admission tube 34.

This separation/concentration filter 32 is equipped with a first outlet 36 and a second outlet 38. The membrane of this filter, made up of a polymer or of cellulose, is hydrophilic and has a porosity of around 0.5 to 5 μm.

Figure 2:
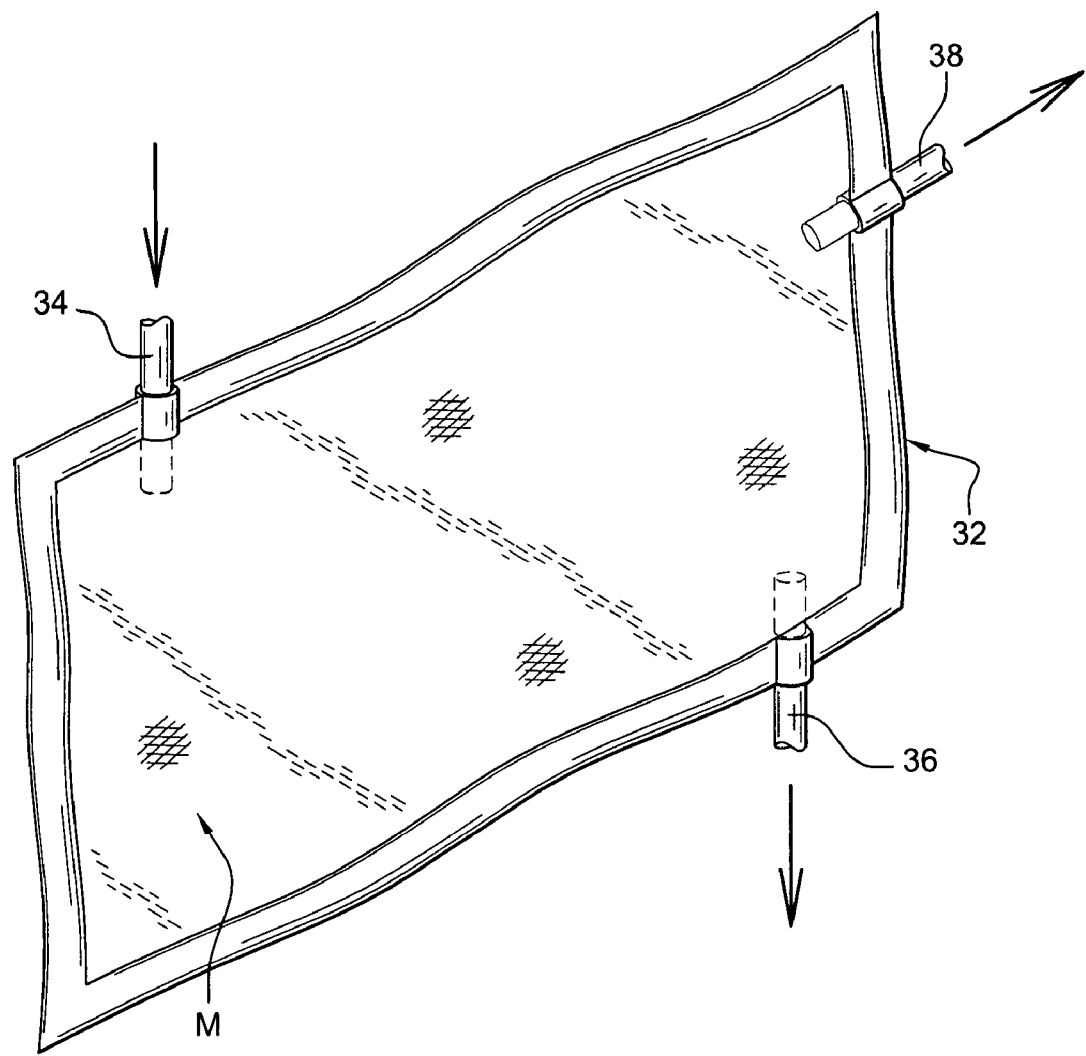
FIG. 2 is a detailed perspective view of the means for separating/concentrating and of the means for recovering the red blood cells on one side and the haemodilution and anticoagulant liquids on the other.

FIG. 2 usefully shows that the separation/concentration filter is a flexible pouch integrating a membrane $\underline{M}$ that divides it into two chambers, V1 and V2.

This membrane is able to retain red blood cells in chamber V1 on the inlet side and let other liquids flow through to chamber V2.

For this reason, the first outlet 36 is connected to chamber V1 in its lower part thus enabling the evacuation of concentrated red blood cells that can represent between 50 and 60% of the volume, associated with a fraction of the liquids.

The first outlet 36 is equipped with an opening and closing system 40.

The second outlet is connected to volume V2.

This second outlet is mounted on a penetrative connection piece 42. This connection piece 42 is connected to a connection piece 44 mounted on means 46 for collecting liquids 48, in this case a flexible pouch. This flexible pouch can contain a large volume even though its size has been reduced on the drawings for practical purposes. It must be able to receive any excess haemodilution liquid recovered through filter 32 during a procedure, and not require to be substituted.

These means 46 for collecting liquids are equipped with a suction connection piece 50 which can be fitted with a vacuum source.

The first outlet 36 is connected via an inlet connection piece 52 to collection means 54 for the concentrated blood fraction. These means 54 are in fact a flexible pouch. The inlet connection piece 52 is equipped with a connection which enables simultaneous removal of the pouch and sealing of the said pouch so as to prevent any blood leakage and/or prevent the contact of the concentrated blood fraction contained in the collection means 54 with open air.

Such a pouch, according to this invention, includes a cap with two inverted threads so that when part of the cap is screwed to seal the pouch the very rotation of the cap triggers the disconnection of the connection piece on which it was initially screwed. The pouch remains immobile during this rotating manoeuvre.

Base 12 is also equipped with a connection piece 56 fitted with a valve to break the vacuum inside the base.

This base is also equipped with a connection piece 58 which enables the creation of vacuum inside the base. This connection piece is controlled via opening/closing means 60 connected to a vacuum source.

The head 14 is also equipped with a device for the creation of vacuum in its inner chamber with a connection piece 62 at the top of head 14, themselves connected to opening/closing means 60 connected to a vacuum source The common vacuum source is connected to an interface 66 placed between base 12 and head 14. This interface is tightly joined to base 12 and head 14. This interface 66 is equipped with a gasket for base 12 and a gasket for head 14 as well as with mechanical and removable attachment means 68 to link it with the same base and head.

This interface is fitted with a unique multifunction control 70 that enables a gathering of opening/closing means 40, 60, and 64. In the implementation represented, this control is composed of a duct 72 equipped with a piston fitted with connection pieces, internal ways and appropriate seals, not shown yet in the reach of the man skilled in the art who knows the functionalities required and described above. This piston can be manoeuvred from the outside of the device with a knob 74 showing the necessary indications and markings. It is also connected via a connection piece 76 to a general vacuum source that can be identical to the one used for other needs.

The functioning of the device just described above, is now described in intra-operative use.

The device is connected to a vacuum source via connection piece 76. A pouch 54 is placed inside base 12. This pouch is sterile and connected tightly in a way that enables later disconnection and automatic sterile sealing.

In parallel, a flexible pouch 46 is also connected to connection piece 44, without the requirement for a sterile environment as the fluids recovered are meant to be destroyed. Nevertheless, for practical aseptic, handling reasons, this pouch may also be equipped with a cap identical to that of pouch 54, a cap that enables the sealing of the pouch while simultaneously disconnecting the connection piece to which it is initially screwed.

Connection piece 56 is closed. Knob 74 is manoeuvred into a position that will create a vacuum in base 12 and head 14 through connection piece 62.

Pouch 46 is also connected to a vacuum source via its connection piece 50. This module is symbolized theoretically, and thus simplified, yet in practice, as it is a flexible pouch, it is necessary to place it in a vessel where depression is created in the same way as for base 12. This enables a separation of the walls of the pouch and generates a vacuum in the pouch thus ensuring that it fills up instead of the walls of said pouch sticking to each other.

The practitioner proceeds with the suction of the fluids flowing from the patient with cannula 16.

At the same time, one or more anti-coagulant agents and one or more diluting agents enable a processing of the fluids so as to avoid the degradation of red blood cells.

With the depression, liquids are sucked in by head 14 and flow through connection piece 24 and filter 26 which is able to retain the largest particles, beyond 40 μm.

The filtrate, sucked in by the depression in head 14, is collected in collector 28 before flowing through separation/concentration filter 32.

The red blood cells and a fraction of the liquids are retained by the membrane of this filter and directed, due to the depression generated in base 12, towards pouch 54.

Filtrate 48, which comes from separation/concentration filter 32, which has an average porosity lower than 5 μm, is sucked into pouch 46 because of the depression in said pouch. This filtrate 48 is free of red blood cells.

When pouch 54, which contains the haemodiluted and concentrated blood is full, the knob, activated in the appropriate way, enables to maintain vacuum in head 14 while interrupting the vacuum in base 12.

The depression is also maintained in collection pouch 46. The vacuum in the base is interrupted through manoeuvring connection piece 56.

The mechanical means for fitting head 14 to the top part of interface 66, on the one hand, and for fitting base 12 to the lower part of this interface 66, on the other, make it possible to separate said head and base.

The manoeuvre of connexion 52 on collection pouch 54 makes it possible to close this first pouch and remove it and to immediately replace it with another pouch if necessary.

The head is once again fitted to base 12 and, by moving knob 74, base 12 can be depressed again after the appropriate manoeuvre of connection piece 56 in closing position.

Collector 28 holds a buffer position during this pouch-substitution operation without any interruption for the practitioner.

The pouch containing the concentrated blood can be kept or used immediately for transfusing the blood thus collected to the patient during the procedure, as the blood is perfectly appropriate for this transfusion. One notes that this blood is concentrated and avoids the side effects encountered with previous devices.

Moreover this concentrated blood brings in a cell stock which increases the oxygenation potential of the tissues of the patient's body.

The present invention also plans for a head for drainage and recovery of haemorrhage blood in the postoperative stage.

The elements common to both stages bear the same reference while the new parts are identified by the addition of 100 to the reference number.

In post operative situation, the practitioner has placed a drain to recover haemorrhage blood which is very good quality blood. This blood, which is not subject to coagulation does not require any specific processing except for a filtration through a filter with an average porosity below 40 μm. We know that the volumes collected can vary between 0.5 and 2 litres which is very significant for a patient after an operation.

The blood thus collected, provided it is collected under appropriate aseptic conditions, can be directly injected back to the patient.

Figure 3:
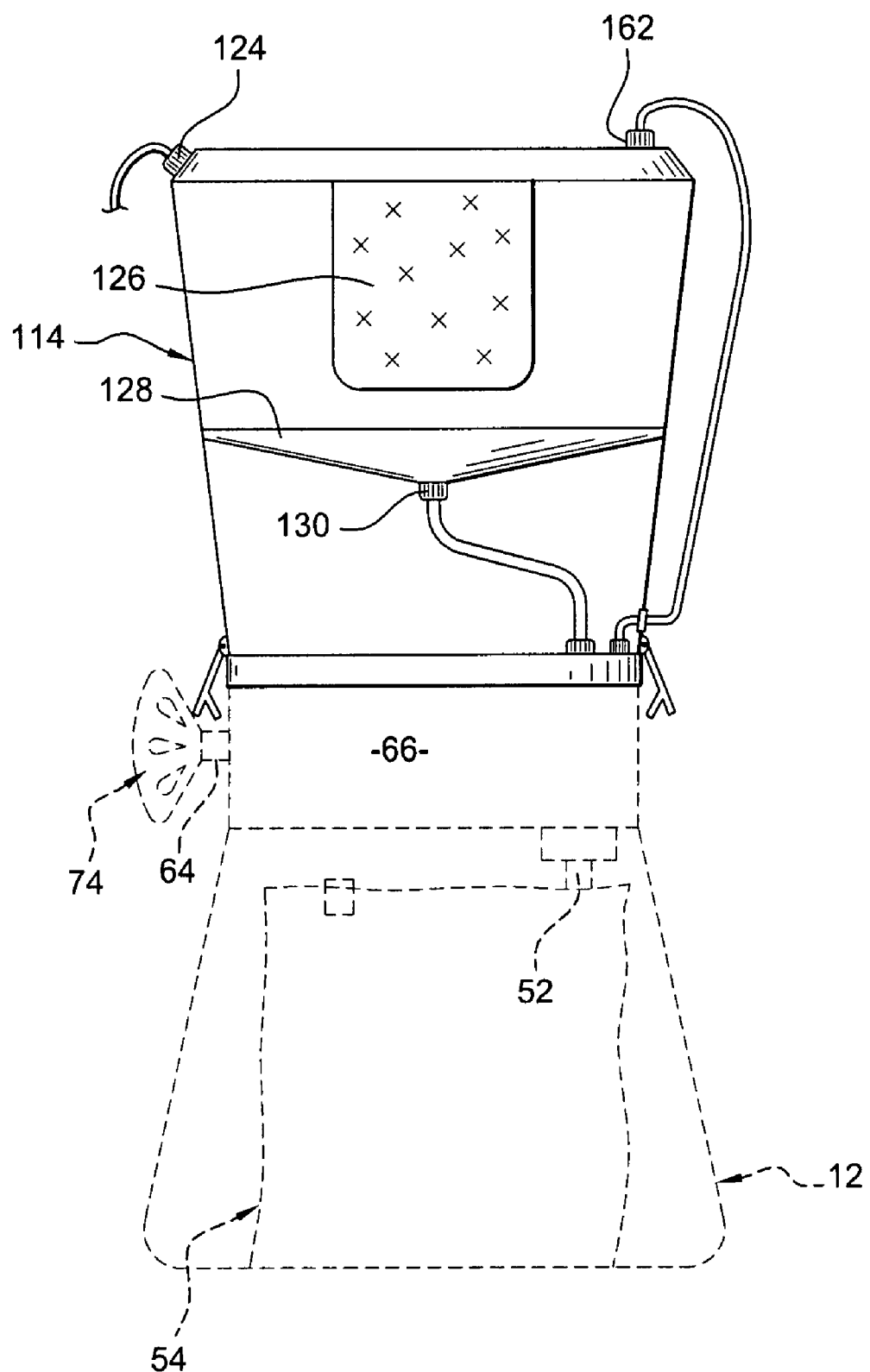
FIG. 3 is a view of the postoperative layer of the device.

In this case, the device represented on FIG. 3 includes an identical base 12, an identical interface 66 and a different head 114.

This head 114 only includes a filter 126 with a mesh of about 40 μm.

Connection piece 162 used to create vacuum in head 114 is retained, still connected by a connection piece 64 to means for opening and closing via the single multifunction control.

Under the filter, a collector 128 is also fitted and runs, via connection piece 130, and through interface 66, directly into base 12, through connection piece 52 whose opening and closing are also controlled by the single multifunction control. The separation/concentration filter is eliminated.

As in the previous case, connection piece 52 receives collection means 54, in this case a flexible pouch.

Connection piece 42 is also eliminated on the head since there are no more means for collecting liquids: as no addition is carried out there is no concentration to effect.

Head 114 is of course fitted with a connection piece 124 to enable its connection to the drain.

The pouch of collection means 54 can be removed to inject back its content as in the previous case.

The depression in head 114 is maintained to recover the fluids from the drain while the vacuum in the base is broken by a manoeuvre at the level of connection piece 56, after manipulating knob 74 in order to interrupt the depression in base 12.

The pouch is simultaneously removed and closed.

A new pouch is positioned and, with connection piece 56 closed, the new depression in the base triggers the filling in of the new pouch.

As previously, one notes that the collector and part of the volume of the head enable to ensure a buffer function and the continuous collection of fluids from the drain while the pouch in base 12 is being changed.

The time for collecting this haemorrhage blood cannot exceed 6 hours after the operation.

It is now possible to recap on the numerous advantages of this device.

One notes that the general architecture enables a standardisation of the various modules, i.e. base 12 and interface 66, which are common, as well as both heads, 14 for the intra operative system and 114 for the post operative one.

These four modules make it possible to respond to many situations.

In the intra operative phase, the device enables a new implementation which is the ongoing processing of the blood to enable its immediate transfusion to the patient.

From a medical point of view, such a device avoids hypocoagulability syndromes due to transfusion of excess quantities of anti-coagulant agents, as well as reducing the transfusion of activated or degraded biological substances likely to generate side effects. Moreover, the blood thus injected back after concentration contributes to the input of a cell stock which increases the oxygenation potential of the tissues of the patient's organism.

The invention authorizes the recovery of pouches containing collected blood or drained fluids in the best conditions, as they are filled, for immediate use, and this without ever interrupting the operation of the device.

The recovery of residual fluids from the concentration stage in the intra operative phase is also carried out directly in flexible pouch-type containers without any manipulation, checking or soiling of any kind.

The device remains compact despite its numerous functionalities which is an asset in a medical environment.

The manipulation with only one single multifunction knob is extremely simple and prevents any error of handling as can happen when several pieces must be manipulated, and in a given order, when there are other more important actions to be carried out at the same time. This eliminates the stress related to the use of such a device, thus enabling the staff to focus on simultaneous or complementary actions.

This device can be improved even more with the integration of an additional filter to remove the leukocytes from the blood which comes from the first 40 μm filter. In this case, such a leukocyte depleting filter is fitted to outlet 36 of separation/concentration filter 32 for the intra operative head and/or to outlet 130 in the case of postoperative head 114.

For the present invention, apart from being fitted with a connection piece which ensures simultaneous sealing upon removal, the recovery pouch can also feature an outlet with a seal to be perforated at time of use.

The invention claimed is:
1. A treatment device for processing haemorrhage fluids of a patient during or after a surgical procedure, comprising:
a head (14, 114) including a means (26, 126, 32) for processing the haemorrhage fluid;
a base module, comprising a base (12);

and a liaison interface (66) comprising a housing and a multifunction control housed within the housing, the housing being attachable to each of the head (14, 114) and the base (12), wherein the base (12) includes a means (54) for sterile collection of at least part of a liquid flowing from the head, wherein the head (14, 114) is removably mounted to the module to enable access to said collection means (54), and wherein said multifunction control includes i) opening/closing means (40) of said base (12), ii) means for the connection of the base (12) to a vacuum source, and iii) means for connection of said at least one head (14) to the vacuum source.

2. The treatment device as in claim 1, wherein the head is one of an intra operative head (14) and a post operative head (114), each of said intra operative head (14) and said post operative head (114) configured to mount on the liaison interface (66) of the base module.

3. The treatment device as in claim 2, wherein the means for processing the haemorrhage fluids from intra operative head (14) are equipped with filtration means (26) and separation/concentration means (32) fitted with a first outlet (36) configured to evacuate red blood cells and a fraction of the liquids and a second outlet (38) connected to means (46) for collecting red blood cell-free liquids.

4. The treatment device as in claim 3, wherein the means for collecting red blood cell-free liquids (48) comprise a pouch equipped with a vacuum unit (50).

5. The treatment device as in claim 4, wherein the means (54) for sterile collection of at least part of the liquid flowing out of head (14) include a flexible pouch removably mounted on an inlet connection piece (52) fitted with a connection configured to be simultaneous sealed upon removal of said pouch in order to prevent any leakage of blood and/or any exposure of a content of said pouch to open air.

6. The treatment device as in claim 3, wherein the separation/concentration means (32) include a flexible pouch including a membrane M for separating the flexible pouch into two chambers V1 and V2, said membrane being configured to retain the red blood cells in chamber V1 on the inlet side under a connection piece (34) and able to let other liquids flow towards chamber V2, the separation/concentration means (32) connected by connection pieces (42,44) to means (46) for collecting red blood cell-free liquids (48).

7. The treatment device as in claim 3, wherein the means (54) for sterile collection of at least part of the liquid flowing out of head (14) include a flexible pouch removably mounted on an inlet connection piece (52) fitted with a connection configured to be simultaneous sealed upon removal of said pouch in order to prevent any leakage of blood and/or any exposure of a content of said pouch to open air.

8. The treatment device as in claim 3, further comprising:
a filter configured for removing leukocytes placed in any of the intra operative head (14) the post operative head (114).

9. The treatment device as in claim 3, further comprising:
a filter configured for removing leukocytes placed in any of the intra operative head (14) the post operative head (114).

10. The treatment device as in claim 3, further comprising:
a filter configured for removing leukocytes placed in any of the intra operative head (14) the post operative head (114).

11. The treatment device as in claim 3, further comprising:
a filter configured for removing leukocytes placed in any of the intra operative head (14) the post operative head (114).

12. The treatment device as in claim 2, wherein the separation/concentration means (32) include a flexible pouch including a membrane M for separating the flexible pouch into two chambers V1 and V2, said membrane being configured to retain the red blood cells in chamber V1 on the inlet side under a connection piece (34) and configured to let other liquids flow towards chamber V2, the separation/concentration means (32) connected by connection pieces (42,44) to means (46) for collecting red blood cell-free liquids (48).

13. The treatment device as in claim 12, wherein the means for collecting red blood cell-free liquids (48) comprises a pouch equipped with a vacuum unit (50).

14. The treatment device as in claim 12, wherein the means (54) for sterile collection of at least part of the liquid flowing out of head (14) include a flexible pouch removably mounted on an inlet connection piece (52) fitted with a connection configured to be simultaneous sealed upon removal of said pouch in order to prevent any leakage of blood and/or any exposure of a content of said pouch to open air.

15. The treatment device as in claim 2, wherein the means (54) for sterile collection of at least part of the liquid flowing out of head (14) include a flexible pouch removably mounted on an inlet connection piece (52) fitted with a connection configured to be simultaneous sealed upon removal of said pouch in order to prevent any leakage of blood and/or any exposure of a content of said pouch to open air.

16. The treatment device as in claim 1, wherein the means (54) for sterile collection of at least part of the liquid flowing out of head (14) include a flexible pouch removably mounted to an inlet connection piece (52) fitted with a connection configured to be simultaneously sealed upon removal of said pouch in order to prevent any leakage of blood and/or any exposure of a content of the collection means (54) to open air.

17. The treatment device as in claim 16, wherein the connection comprises a cap with two inverted threads so that a part of the cap is screwable, and the pouch is sealable by a rotation of the cap that simultaneously disconnects the cap from the connection piece (52).

18. The treatment device as in claim 1, further comprising:
a filter for removing leukocytes placed in the head (14, 114).

19. The treatment device as in claim 1, wherein the liaison interface is configured to rest on said base (12) and support the head (14, 114) on a first interface of said liaison interface, the first interface configured for removably receiving the head, and a second interface opposite the first interface configured for removably mounting to the base (12).

20. The treatment device as in claim 19, wherein the first interface includes a first gasket for the head (14, 114), and the second interface includes a second gasket for the base (12).

* * * * *